(12) United States Patent
Yunoki et al.

(10) Patent No.: US 8,105,629 B2
(45) Date of Patent: Jan. 31, 2012

(54) COLLAGEN GEL AND PROCESS OF PRODUCING THE SAME

(75) Inventors: Shunji Yunoki, Ibaraki (JP); Nobuhiro Nagai, Hokkaido (JP)

(73) Assignee: Ihara & Company Ltd., Hokkaido (JP)

( * ) Notice: Subject to any disclaimer, the term of this patent is extended or adjusted under 35 U.S.C. 154(b) by 0 days.

(21) Appl. No.: 10/547,309

(22) PCT Filed: Feb. 24, 2005

(86) PCT No.: PCT/JP2005/003552
§ 371 (c)(1),
(2), (4) Date: Aug. 29, 2005

(87) PCT Pub. No.: WO2005/079879
PCT Pub. Date: Sep. 1, 2005

(65) Prior Publication Data
US 2006/0177492 A1 Aug. 10, 2006

(30) Foreign Application Priority Data
Feb. 25, 2004 (JP) ................ 2004-049332
Sep. 29, 2004 (JP) ................ 2004-284993

(51) Int. Cl.
*A61L 15/32* (2006.01)
*A61F 13/00* (2006.01)
*C07K 14/78* (2006.01)
*C07C 267/00* (2006.01)

(52) U.S. Cl. ........ 424/485; 424/445; 424/422; 530/356; 560/334

(58) Field of Classification Search ................. 424/485, 424/445, 422; 560/334; 530/356
See application file for complete search history.

(56) References Cited

U.S. PATENT DOCUMENTS

| | | | |
|---|---|---|---|
| 4,424,208 A | 1/1984 | Wallace et al. | |
| 4,725,671 A * | 2/1988 | Chu et al. | 530/356 |
| 5,648,208 A * | 7/1997 | Fourcart et al. | 435/5 |
| 5,714,582 A | 2/1998 | Wolfinbarger | |
| 6,335,007 B1 * | 1/2002 | Shimizu et al. | 424/78.08 |
| 6,541,023 B1 * | 4/2003 | Andre et al. | 424/422 |
| 6,660,280 B1 | 12/2003 | Allard et al. | |
| 2004/0009600 A1 * | 1/2004 | Bowlin et al. | 435/395 |
| 2004/0146543 A1 * | 7/2004 | Shimp et al. | 424/423 |

FOREIGN PATENT DOCUMENTS

| CA | 2485914 A1 | 11/2003 |
|---|---|---|
| JP | 8283667 | 10/1996 |

(Continued)

OTHER PUBLICATIONS

Wikipedia, definition of fibrosis, http://en.wikipedia.org/wiki/Fibrosis, printed on Jan. 23, 2007.*

(Continued)

*Primary Examiner* — Rosanne Kosson
(74) *Attorney, Agent, or Firm* — Novak Druce + Quigg LLP (57) ABSTRACT

The present invention relates to a process of producing a collagen gel comprising collagen fibers cross-linked with each other by a cross-linking agent on the way of fibrosis of collagen, and a collagen gel comprising the cross-linked collagen fibers obtained by the process.
The collagen gel comprising cross-linked collagen fibers of the present invention has high strength and thermal stability and can be widely used as cell carriers and medical materials.

11 Claims, 4 Drawing Sheets

FOREIGN PATENT DOCUMENTS

| | | |
|---|---|---|
| JP | 11197234 | 7/1999 |
| JP | 2002080501 | 3/2002 |
| JP | 200513457 | 1/2005 |

OTHER PUBLICATIONS

Berenbaum, "Synergy, additivism and antagonism in immunosuppression," Clin exp Immunol 28:1-18, 1977.*

Kadler et al., "Collagen fibril formation," Biochem J 316(1):1-11, 1996.*

Sung et al., "Crosslinking of biological tissues using genipin and/or carbodiimide," J Biomed Mater Res 64A:427-438, Wiley Periodicals, Inc., 2003.*

Sigma-Aldrich, Learning Center, Buffer Reference Center, http://www.sigmaaldrich.com/life-science/core-bioreagents/biological-buffers/learning-center/buffer-reference-center.html, printed from the Internet Nov. 13, 2008, data reprinted from Dawson et al., Data for Biochemical Research 3rd ed., Oxford Science Publ., 1986.*

Yunoki et al. ("Novel biomaterial from reinforced salmon collagen gel prepared by fibril formation and cross-linking," J Biosci and Bioengineering 98(1):40-47, published Aug. 5, 2004.*

Yoshihiro Nomura et al., The Physiochemical Property of Shark Type I Collagen Gel and Membrane, J. Agric. Food Chem., vol. 48, 2000, p. 2028-2032.

Joanne Kelly et al., Fibril-forming Collagens in Lamprey, The Journal of Biological Chemistry, vol. 263, No. 2, 1988, p. 980-987.

T. Koide and M. Daito, Effects of Various Collagen Crosslinking Trechniques on Mechanical Properties of Collagen Film, Dental Mat. J., 16(1): 1-9 (1997).

L.H.H. Olde Damink, P.J. Dijkstra, M.J.A. Van Lyun, P.B. Van Wachem, P.Nieuwenhuis and J. Feijen, , "Glutaraldehyde as a Crosslinging Agent for Collagen-Based Biomaterials," J. Mater. Sc. Mater Med., 6, (1995) 460.

W.F. Daamen, H.T. Van Moerkerk, T.as, L. Buttafoco, A.A. Poot, J.H. Veerkamp and T.H. Van Kuppevelt, Biomaterials, 24 (2003) 4001.

Tetsushi Taguchi, et al., "An Improved Method to Prepare Hyaluronic Acid and Type II Collagen Composition Matrices," Wiley Periodical, Inc., 2002.

Yunoki S et al; "Novel Biomaterial from Reinforced Salmon Collagen Gel Prepared by Fabril F . . . ";Journal of Bioscience and Bioengineering; Nol. 98, No. 1, 40-47; 2004.

Communication (Search Report) from the European Patent Office dated Aug. 3, 2010 for EP Application No. 05719866.5.

Gelman et al., J Biol Chem 254, 180-186 (1979).

Williams et al., J Biol Chem 253, 6578-6585 (1978).

* cited by examiner

COLLAGEN GEL AND PROCESS OF PRODUCING THE SAME

This application is a 35 U.S.C. §371 U.S. National Stage Application of International Application No. PCT/JP2005/003552, filed on Feb. 24, 2005, claiming the priority of Japanese Patent Application No. 2004-49332, filed Feb. 25, 2004 and Japanese Patent Application No. 2004-284993, filed Sep. 29, 2004, the entire disclosures of which are incorporated herein by reference in their entireties.

TECHNICAL FIELD

The present invention relates to a collagen gel and a process of producing the same. More particularly, the present invention relates to a collagen gel obtained by cross-linking collagen fibers derived from fishes and a process of producing the same, and also to a cell carrier, a medical material, a wound-dressing material, an artificial dura mater and a drug delivery system (DDS) material each using the collagen gel.

BACKGROUND ART

The term "collagen" is defined as protein or glycoprotein, which has at least partially a helical structure (collagen helix) This is a triple helix composed of three polypeptide chains, wherein each polypeptide chain has a molecular weight of about 100,000 in which a glycine residue appears every three residues and proline and hydroxyproline residues appear as other amino acid residues at high frequency. Collagen can be extracted in a large amount from the tissues of an invertebrate or a vertebrate animal, in particular from the skin thereof. It has been reported that collagen molecules can be divided into 19 different types depending on their different structures and the collagen molecules classified in the same type may include several different molecular species.

Particularly, types I, II, III and IV of collagen have been mainly used as sources of biomaterials. The type I can be found in most of the connective tissues and is the most abundant collagen type in a living organism, particularly in the tendon, corium and bone. Industrially, in many cases, collagen can be extracted from those portions. The type II is a collagen that forms a cartilage. The type III is found in a small quantity in the same portions as those of the type I. The type IV is a collagen that forms a basal membrane. The types I, II and III are present as collagen fibers in a living organism, and have a main function of maintaining the strength of a tissue or of an organ. The type IV, which does not have ability for fibrogenesis, forms a net-like assembly constructed of four molecules and may take part in cell differentiation in a basal membrane. In the present specification, hereinafter, the term "collagen" refers to one of the types I, II and III or a mixture of two or more of them.

A collagen fiber is a self-assembly of the collagen molecules and has a specific fiber structure in which the collagen molecules are packed in series and parallel. Industrially, using acid, alkali or a proteolytic enzyme, solubilized collagen can be prepared from collagen fibers in tissues.

The solubilized collagen may be divided into assemblies of not more than several collagen molecules and then dissolved in water or an aqueous salt solution to prepare a uniform transparent solution. It is known that collagen molecules, which are once solubilized, will regenerate collagen fibrils in vitro under certain conditions. This phenomenon is called fibril formation (fibril formation or fibrillation) and the detailed characteristic features thereof are described in Biochemical Journal 316, p. 1-11 (1996).

When collagen is heated, the triple helix structure of collagen comes loose and then each polypeptide chain provides a thermal denatured product in a random coil form. The temperature at which such a structural change occurs is called "denaturation temperature", while the thermal denatured product is called "gelatin". It is known that gelatin has higher water solubility than that of collagen and high sensitivity to in vivo protease. Depending on the solvent conditions, gelatin is known to partially recover a collagen helical structure. Even though gelatin has lost its ability of forming a collagen fiber, it is known that it may recover its ability of forming a collagen fiber by partially recovering its collagen helical structure.

The denaturation temperature of collagen is the lowest in a solution state. In addition, collagen is generally obtained from a biological source and the denaturation temperature of collagen obtained from a living organism is allegedly closely associated with environmental temperatures surrounding the organism. Denaturing temperature of collagen of mammals in an aqueous solution is about 38° C. The denaturation temperature of collagen of fishes is generally lower than that of the collagen of mammals and in particular fishes living in cold currents, such as salmon, may each have a denaturation temperature of lower than 20° C.

Collagen has superior moisture retention and is cheaper than other biogenetic humectants such as hyaluronic acid because of its higher yield. Therefore, it is effectively used as a raw material in cosmetics. In addition, collagen has many excellent properties such as facilitating adhesion and growth of cells, low antigenicity, high bioaffinity and biodegradability, so that it has been used in various kinds of applications, such as materials for experiments on cells and medical materials. When collagen is used in any of those purposes, it may be used in any of various forms such as an aqueous solution, floc, film, sponge and gel depending on the applications. In particular, collagen gel is effectively used for cell carriers, medical materials, and soon. In recent years, extensive studies have been conducted on collagen gel as an important material in regenerative medicine. Processes of producing collagen gel can be divided into three types as follows.

1. A process in which a cross-linking agent is introduced into a collagen solution to gelatinize the solution.
2. A process in which a collagen solution is irradiated with luminous rays inducing cross-link to gelatinize the solution.
3. A process in which a neutral buffer is added to a collagen solution to induce fibril formation of collagen to obtain a gel constructed of a collagen fibril network.

Regarding the above-mentioned process 1, for example, there are disclosed a collagen gel formed product for ophthalmology obtained by mixing a chemical cross-linking agent in a collagen solution to gelatinize the solution (JP-A-11-197234) and a gel for tissue-regenerating matrix in which a mixture solution of glycosaminoglycan and collagen cross-linked with aqueous carbodiimide (JP-A-2002-80501). Regarding the above-mentioned process 2, for example, there is a report that a collagen solution is gelatinized when it is sufficiently substituted with nitrogen and then irradiated with ultraviolet rays (Biochimica Biophysica Acta 229, p. 672 to 680 (1971)). Regarding the above-mentioned process3, for example, a gel constructed of a collagen fiber network is reported which is obtained by mixing an aqueous solution of shark-originated collagen with a neutral buffer to induce fibrosis of collagen (Journal of Agricultural Food Chemistry 48, P. 2028 to 2032 (2000)).

The collagen gels made by the above three gelation processes are lacking in sufficient thermal stability. In a certain application, collagen may be denatured to cause softening or dissolving of the gel to thereby become unusable. In addition, the strength of the gel is insufficient, so that in a certain application the gel may be constricted and degraded to thereby become unusable.

Therefore, in recent years, in view of improving the strength of a collagen gel, there has been disclosed technology to bring a collagen gel prepared by fibril formation of an acidic collagen solution into contact with a protein-linking agent (JP-A-8-283667). However, in this technology, the cross-linking takes place only on the surface of the collagen fiber fibril and the cross-linking agent does not reach the central part of the gel, resulting in poor improvement in strength. Consequently, there is a problem that the technology does not attain a substantial improvement with respect to the thermal stability of gel.

Any one of the cross-linking agents known in the art has not succeeded in solving an essential problem in that it does not act on the inside of a helix of a collagen molecule but act on between the collagen molecules and another problem that the cross-linking agent hardly exerts its effect on the inside of a collagen gel. Therefore, an improvement in thermal stability has not been attained sufficiently. In other words, there has been no disclosure with respect to a technology that imparts higher thermal stability to a collagen gel than those of the collagen gels prepared by the above three gelation processes.

Furthermore, most of collagen as a raw material for a collagen material has been conventionally collected from the tissues of domestic animals, such as bovine hide. However, in recent years, the issue of BSE (bovine spongiformencephalopathy) has been elicited. It has been pointed out that a risk of infections of pathogens to humans lie latent in collagen products using raw materials from domestic animals including bovine hide. From the viewpoints of safety, quantity of natural resources, and so on, fish-origin collagen comes into the limelight as any of cosmetic and food materials. Thus, it becomes important to use fish-origin collagen obtained from fishes having a low denaturation temperature as a raw material of collagen.

However, though the fish-origin collagen has a low risk, due to its low denaturation temperature, its thermal stability as a material is insufficient in many cases. Therefore, comparing with collagen originated from a domestic animal, the fish-origin collagen may be disadvantageous as a raw material of a cell carrier or of a medical material.

The above-mentioned problems with respect to insufficient thermal stability or strength, and the like in the conventional process of producing collagen have restricted a wide variety of applications of general collagen gels originated from domestic animals to medical materials. Furthermore, for using the gels as medical materials, the gels are often requested to be stable at least at a body temperature of 37° C., so that the conventional process was insufficient for a stabilization approach for collagen gels derived from fishes.

SUMMARY DISCLOSURE OF THE INVENTION

Accordingly, an object of the present invention is to provide: a collagen gel, particularly one originated from fishes, having high strength and thermal stability, which can be widely used as cell carriers and medical materials; a process of producing the collagen gel; and a collagen sheet obtained by such a process and a use thereof.

By the conventional process of producing a collagen gel, a collagen gel having insufficient strength and thermal stability is obtained. Depending on its applications, softening and dissolving of the gel due to denaturation may occur, thereby making it impossible to use the collagen gel. In addition, it is difficult to provide fish-origin collagen gel with high thermal stability sufficient to be used as a medical material.

As result of intensive studies to solve the above problems, the present inventors have finally attained the present invention by finding out that a collagen material which is extremely useful as a cell carrier, a medical material, a wound-dressing materials, an artificial dura mater and a drug delivery system (DDS) material can be obtained by causing a cross-linking reaction between collagen fibrils on the way of fibril formation of collagen to thereby simultaneously attain extensive improvements in both strength and thermal stability of a collagen gel, which have been hardly attained by the conventional method.

That is, the present invention provides the following collagen gel; a process of producing the same; and a cell carrier, a medical material, a wound-dressing material, an artificial dura mater and a drug delivery system (DDS) material, each of which uses the collagen gel.

1. A collagen gel characterized by comprising collagen fibrils cross-linked by a cross-linking agent.
2. The collagen gel according to 1 above, wherein the collagen is derived from fishes.
3. The collagen gel according to 1 above, wherein the cross-linking agent is water-soluble carbodiimide.
4. A process of producing a collagen gel comprising cross-linked collagen fibrils characterized by cross-linking collagen fibrils with each other by cross-linking agent on the way of fibril formation of collagen fibers.
5. The process of producing a collagen gel according to 4 above, including mixing a collagen solution with a solvent which induces fibrosis and a solution of cross-linking agent.
6. The process of producing a collagen gel according to 4 or 5 above, wherein collagen obtained from fishes is used.
7. The process of producing a collagen gel according to 5 above, wherein the solvent inducing fibrosis is an aqueous salt solution having buffering ability selected from the group consisting of phosphate, acetate, carbonate and Tris.
8. The process of producing a collagen gel according to 5 above, wherein the cross-linking agent used is a solution prepared by dissolving water-soluble carbodiimide in a solvent that induces fibrosis.
9. The process of producing a collagen gel according to 5 above, wherein the collagen solution has a collagen concentration of 0.01 to 3.0 (w/v)%.
10. The process of producing a collagen gel according to 5 above, wherein the cross-linking agent used is in the range of 15 to 80 mM as a final concentration of the cross-linking agent in the collagen gel.
11. The process of producing a collagen gel according to 5 above, wherein mixing the collagen solution with the solvent inducing fibrosis and the solution of cross-linking agent is carried out at a denaturation temperature of collagen of +5° C. or lower.
12. The process of producing a collagen gel according to 11 above, wherein, after mixing of the collagen solution, and the solvent inducing fibrosis and the solution of cross-linking agent, the resulting mixture is incubated for at least one hour at a denaturation temperature of collagen of +5° C. or lower.
13. A collagen gel, produced by a process according to any one of 4 to 12 above.
14. A collagen sheet, obtained by removing the solvent from the collagen gel according to 13 above.
15. A cell carrier or a medical material, comprising the collagen gel according to any one of 1 to 3 and 13 above.
16. A cell carrier or a medical material, comprising the collagen sheet according to 14 above.

17. A wound-dressing material, comprising the collagen sheet according to 14 above.

18. An artificial dura mater, comprising the collagen sheet according to 14 above.

19. A drug delivery system material, comprising the collagen sheet according to 14 above.

An object of the present invention is to provide a collagen gel, characterized by attaining synergistic improvements of mechanical strength and thermal stability of a collagen gel by means of cross-linking and fibrosis such that a cross-linking reaction occurs between fibers on the way of fibrosis of collagen; and a producing process thereof.

DETAILED DISCLOSURE OF THE INVENTION

Hereinafter, the present invention will be described in detail.

The collagen used in the present invention is not limited to a specific type as far as it has fibrosis ability. In terms of industrial use, type I collagen or collagen mainly containing type I collagen is preferable because of its higher yield.

Collagen used in the present invention is not limited to one having a particular molecular structure as far as it has fibrosis ability. There is a report that non-helical regions (telopeptides) on both ends of a collagen molecule have antigenicity. Even though those regions should be removed in certain uses, there is no need to remove telopeptides as far as the fibrosis ability is retained.

The collagen used in the present invention is not particularly limited to a specific one with respect to its denaturation as far as it retains fibrosis ability. It is known that collagen once denatured may partially recover its collagen helical structure and thereby recover its fibrosis ability. For attaining the present invention, from the viewpoint of fibrosis ability, the collagen has preferably a helical rate (%) of 50 or more. The above term "helical rate (%)" is synonymous with the term "helix-recovering rate (%)" described in Journal of Food Chemistry 60, p. 1233 (1995). In other words, the term "helical rate" refers to a helix-recovering rate (%) calculated from the value of specific optical rotation determined by an optical rotation meter.

Collagen used in the present invention is not limited to a specific one with respect to its origin as far as it retains fibrosis ability. However, from the viewpoint of the quantity of natural resources and the yield of collagen, collagen originated from the corium of vertebrates is preferably used. Of those, collagen derived from the corium of fishes such as salmon skin, shark skin, tuna skin, cod skin and fluke skin is more preferably used, wherein possibility of containing pathogens such as BSE is latently less than that in domestic animals. Of those, the salmon skin is particularly preferably used.

The term "collagen fiber(s)" used in the present invention means a filamentous structure as shown in a scanning electron micrograph in the document (Journal of Agricultural Food Chemistry 48, P. 2028-2032 (2000)).

The cross-linking agent used in the present invention is not limited to a specific one as far as it is capable of cross-linking proteins and retains water solubility. Cross-linking agents for proteins are described in the document (Biomaterials 18, p. 95-105 (1997)) in detail. Of those, aldehyde-, carbodiimide-, epoxide- and imidazole-based cross-linking agents are preferably used in terms of economical efficiency, safety and operability. In particular, it is preferable to use a water-soluble carbodiimide such as 1-ethyl-3-(3-dimethyl aminopropyl) carbodiimide/hydrochloride or 1-cyclohexyl-3-(2-morpholinyl-4-ethyl)carbodiimide/sulfonate in a form of a solution in a solvent inducing fibrosis as described later.

When the cross-linking agent used in the present invention is water-soluble carbodiimide, the agent may be coexistent with N-hydroxy succinimide to increase cross-linking efficiency.

The process of producing a collagen gel of the present invention is characterized by causing a cross-linking reaction on the way of fibrosis of collagen. As specific processes for attaining such a characteristic feature of the present invention, the following three processes can be given.

A. A process wherein a collagen solution is mixed with a solution of a cross-linking agent using a solvent inducing fibrosis.

B. A process wherein a collagen solution is mixed with a solvent inducing fibrosis simultaneously with or followed by the addition of a cross-linking agent solution.

C. A process wherein a cross-linking agent is added to a collagen solution and then a solvent inducing fibrosis is mixed therewith.

Any one of those processes initiates a cross-linking reaction on the way of fibrosis of collagen to cause cross-linking between collagen molecules and between collagen fibers. This reaction results in synergistic effects of collagen fibrosis and cross-linking, which enables to obtain a collagen gel having desired strength and thermal stability that have been hardly attained by the conventional process. From the viewpoint of operability, it is particularly preferable to produce a collagen gel by the process A.

A pH value of the collagen solution used for the production of the collagen gel of the present invention varies depending on the process of producing collagen raw materials. Collagen can be mainly divided into acid-soluble collagen to be extracted by an aqueous acidic solution and alkali-soluble collagen to be extracted by an aqueous alkali solution. When the collagen solution used in the present invention is an acid-soluble collagen solution, the solution has a pH value of preferably 2.0 to 6.0. A pH value of less than 2.0 is not preferable because collagen molecules may be hydrolyzed. A pH value of higher than 6.0 is not preferable because collagen may not be solubilized sufficiently. On the other hand, when the collagen solution used in the present invention is an alkali-soluble collagen solution, it is preferable that the pH of the solution be in the range of 5.5 to 10. A pH value of less than 5.5 is not preferable because collagen may not be solubilized sufficiently. A pH value of higher than 10 is not preferable because collagen molecules may be hydrolyzed.

As a solvent of a collagen solution used in the production of collagen of the present invention, if it is an acetic solvent, it is preferable to use those extensively used industrially, for example, water or an aqueous solution of hydrochloric acid, acetic acid, citric acid and fumaric acid for safety in view of the final usage. When the solvent is neutral to alkaline, because of the same reasons as those described above, water or an aqueous solution of phosphate, acetate, Tris or the like is desirable.

A solute concentration of the collagen solution used in the production of a collagen gel of the present invention is not particularly limited as far as the solvent can be provided with a pH value that allows collagen used to be soluble. However, when the solute concentration is too high, depending on the solute to be used, there may be some cases where, which are not preferable, the solute may be difficult to provide pH within a desired range, the fibrosis of collagen may be inhibited or the physical properties such as cellular adhesiveness of a gel to be obtained may be inhibited. Therefore, the solute concentration is preferably 1.0 M or less, more preferably 0.50 M or less.

To a collagen solution to be used in the production of a collagen gel of the present invention, various functional substances may be added for the purpose of further increasing the functions of the collagen gel as far as the addition does not inhibit an effect of the present invention to obtain a collagen gel having high thermal stability. Specific examples of the functional substances include functional proteins such as cell growth factors; and functional polysaccharides such as hyaluronic acid, chondroitin sulfate, polylactide, β1-3 glucan, chitin and chitosan.

A collagen solution used in the production of a collagen gel of the present invention has a collagen concentration of preferably 0.01 to 3.0 (w/v)% in terms of the solubility of the collagen, the viscosity of the solution or the physical properties of the gel. A collagen concentration of less than 0.01 (w/v)% is not preferable because the strength of the gel may be insufficient. A collagen concentration of higher than 3.0 (w/v)% is not preferable because the production of the gel may become difficult because of excessive viscosity of the collagen solution. Therefore, the collagen concentration is preferably in the range of 0.05 to 2.0 (w/v)%.

For the concentration of a cross-linking agent used in the production of a collagen gel of the present invention, a final concentration of the cross-linking agent in the collagen gel is more important rather than the concentration of a cross-linking agent solution. From the viewpoint of cross-linking degree and cross-linking rate, the final concentration of the cross-linking agent is preferably in the range of 15 mM to 80 mM. A final concentration of the cross-linking agent of less than 15 mM is not preferable because the strength and thermal stability of the gel may become insufficient because of lack of the cross-linking degree. A final concentration of the cross-linking agent of higher than 80 mM is not preferable because the strength and thermal stability of the gel may become insufficient because the coexistence of the cross-linking agent remarkably interfere with collagen fibrosis.

A solvent used in the production of a collagen gel of the present invention to induce the fibrosis of collagen is not specifically limited. However, in consideration of a final application such as a cell carrier or a medical material, a preferable solvent is an aqueous salt solution having buffering ability such as a solution of phosphate, acetate, carbonate, Tris or the like which has no or less cytotoxicity and is widely applied for industrial uses. A pH value suitable for fibrosis of collagen, which varies depending on the kind of the collagen, is within the range of 5 to 9 in many cases. A phosphate having high buffering ability in the range is particularly preferably used. The solute concentration in the solvent is based on the solute concentration in a solvent for a collagen solution used in the production of a collagen gel of the present invention.

An operation of mixing a collagen solution with a solution that induces fibrosis or with a cross-linking agent solution is carried out while the temperatures of the respective solutions are kept not to substantially exceed the denaturation temperature. In particular, the temperature of the solution after mixing is important. If the temperature of the mixture solution is much higher than the denaturation temperature of collagen, the denaturation of collagen may occur and the fibrosis ability thereof may decrease even though a cross-linking reaction occurs. In this case, therefore, the effect of the present invention for producing a collagen gel having high gel strength and thermal stability may not be obtained sufficiently. Thus, the case is not preferable. Preferably, the temperature of the mixture solution is five degrees above the denaturation temperature of the collagen used or lower, more preferably equal to or lower than the denaturation temperature of the collagen used.

The denaturation temperature of the collagen is a value determined from variations in optical rotation of a collagen solution when the collagen solution is heated in a stepwise manner, which is described in Journal of Food Chemistry 60, p. 1233 (1995).

In an operation of mixing a collagen solution with various kinds of solutions to cause fibrosis and cross-linking, a mixing method of these solutions is not limited to a specific one. However, before the fluidity of the solution is lost as a result of gelation of the solution by fibrosis, they are preferably mixed as uniformly as possible. Preferably used is a method comprising introducing a mixture solution into a container and shaking the container by hands or by a shaker or a method comprising stirring a solution mechanically with a magnetic stirrer, a vaned stirring rod or the like.

After a collagen solution is mixed with various solutions for causing fibrosis and cross-linking, the resulting mixture solution is incubated for causing fibrosis and cross-linking reaction sufficiently. It is preferable that the incubation may be carried out for at least one hour with the object of providing the collagen with higher gel strength and thermal stability. From the view point of preventing collagen from denaturation, the incubation temperature corresponds to five degrees above the denaturation temperature of collagen or lower, more preferably the denaturation temperature of collagen or lower.

The collagen gel of the present invention obtained by the process described above has high mechanical strength and at the same excellent thermal stability. Thus, application for any use, which has been hardly attained by the conventional collagen gel, will be expected. In addition, a collagen gel having mechanical strength and thermal stability enough to be applied in cell carriers or medical materials such as those used in regenerative therapy can be produced using fish-origin collagen having a low denaturation temperature.

Furthermore, a collagen sheet can be prepared by removing a solvent from the collagen gel of the present invention obtained as described above. A method of removing the solvent may be air drying or a press. Of those, air drying is preferably used because additional cross-linkage can be introduced during the step of removing the solvent and the operation thereof is simple with little damage on a sample.

The step of removing the solvent from the collagen gel by means of air drying is carried out at a temperature equal to or lower than a melting point of the gel. The air drying is not preferably carried out at a temperature higher than the melting point because the gel may be denatured by heat and shrunk. An excessively low temperature is not preferable because the solvent evaporation takes too much time. Therefore, the temperature is preferably in the range of 10 to 50° C., more preferably 25 to 40° C.

The step of removing the solvent from the collagen gel by a press is carried out under a pressure of 1 kPa to 10 MPa. A pressure less than 1 kPa is not preferable because the strength of gel exceeds the pressure and the removal of the solvent may be insufficiently carried out. A pressure more than 10 MPa is not preferable because the gel may be broken by rapid distortion. The pressure is preferably in the range of 10 kPa to 1 MPa.

In the step of removing a solvent from the collagen gel by a press, an absorbent material may be placed between a press machine and the gel to increase compactibility. Paper, cotton, or the like, which is cheap and has excellent water absorbing property, may be preferably used for the absorbent material, but not limited thereto. For preventing adhesion between the gel and the absorbent material, a hydrophobic filter such as a Teflon-made filter may be sandwiched therebetween.

The collagen sheet of the present invention obtained by the above method has an equally high mechanical strength and excellent thermal stability as the collagen gel. Therefore, application for any use, which has been hardly attained by the conventional collagen sheet, will be expected. In addition, a collagen sheet having mechanical strength and thermal stability enough to be applied to medical materials such as wound-dressing materials, artificial duramaters, and drug delivery system (DDS) materials can be produced using fish-origin collagen having a low denaturation temperature.

BEST MODE FOR CARRYING OUT THE INVENTION

Hereinafter, the present invention will be more specifically described with reference to examples and comparative examples. However, the present invention is not limited to the scope of the description below.

At first, various methods for measurement will be described.

1. Observation of Collagen Fibers

By the following procedures, collagen fibers in a collagen gel were observed. A collagen gel was immersed in a 2.5 (w/v)% glutaraldehyde aqueous solution for 24 hours and then immersed in 20%, 50%, 75%, and 99 (v/v)% ethanol aqueous solutions successively for 30 minutes per solution to dehydrate the collagen gel. Then, it was immersed in isopentyl acetate twice for 15 minutes each time, and subsequently underwent critical point drying with $CO_2$. The dried collagen gel was coated with Au using an ion coater (E-1010, manufactured by Hitachi) and then provided as a sample of a scanning electron microscope (SEM). SEM observation was carried out using JSM-6500F manufactured by JEOL at a magnification of 15,000.

2. Measurement of Gel Strength of Collagen Gel

The gel strength of a collagen gel was determined by the following procedures.

A collagen gel was prepared so as to be 5 to 7 mm in thickness on a cell-culture polystyrene petridish (manufactured by IWAKI) of 35 mm inner diameter. A disk probe having an inner diameter of 20 mm was pressed into the gel at a rate of 50 mm/min. A stress (g) at the time of further pressing the probe by a constant depth (1.3 mm) after detecting the stress was measured using a rheometer (CR-200D, manufactured by San Kagaku). The average value of stress (g) was calculated from the measurement results of three gels to determine a gel strength.

3. Measurement of Melting Point of Collagen Gel

The melting point of a collagen gel was measured by the following procedures to evaluate the thermal stability of the collagen gel. That is, a gel was prepared such that it would have a height of 40±5 mm in a glass test tube of 15 mm inner diameter, followed by being placed in a water bath. The water bath was heated stepwise by every 1° C. from 20° C. (a retaining time at each temperature: 30 minutes). Then, the thermal stability of the gel was evaluated from a temperature at which the gel dissolved. The dissolution of gel may gradually occur at temperatures ranging over two or three degrees. The temperature at which almost half of the gel volume dissolved was determined as a melting point (° C.).

4. Cell Proliferation Assay on Collagen Gel (1) Cell Culture

Human periodontal ligament cells (hPDL cells) were obtained by the following procedures. From the dental root of an extracted tooth, hPDL cells were collected and incubated in a Dulbecco-modified Eagle's medium (DMEM, manufactured by Nissui) added with 10% serum (Fetal Bovine Serum, manufactured by GIBCO). Culture medium was replaced every two days and when the cells reached semi-confluent, the cells were dispersed by a 0.02% trypsin and 0.25% EDTA solution and then transferred to a new plate so as to be $5 \times 10^3$ cells/$cm^2$ for successive culture.

hPDL cells having a passive number of 10 to 15 were used for the collagen gel culture. The cells attached on the collagen gel were observed by the following procedures to evaluate the cell adhesion on the collagen gel. A gel was prepared in a cell-culture polystyrene petridish (12 wells, manufactured by NUNC) of 16 mm inner diameter so as to obtain a gel volume of 750 µl. After placing phosphate buffer saline (−) (PBS) on the gel, it was incubated for 40 minutes at 37° C., followed by removing PBS. This procedure was repeated four times to remove salt, unreacted cross-linking agent, and so on in the gel. 10% serum-containing DMEM was placed on the gel, immediately before the cell incubation, and it was incubated for 40 minutes at 37° C. After the medium was removed, the gel was washed. On the washed collagen gel, hPDL cells were seeded so as to be $5 \times 10^3$ cells/$cm^2$ and then incubated in a 5% $CO_2$ incubator at 37° C. using 10% serum-containing DMEM as a medium. The medium was replaced every two days.

(2) Cell Proliferation Assay

A test for proliferation activity was performed using a proliferation assay kit (CellTiter 96 AQueous Non-Radioactive Cell Proliferation Assay, manufactured by Promega). After incubation for predetermined days, 1 mL of a proliferation assay solution was added to the medium, followed by incubating in a 5% $CO_2$ incubator for 60 minutes. After incubation, 200 µL of a supernatant was collected and transferred into a 96-well plate (manufactured by NUNC), followed by measuring absorbance at 490 nm by a plate reader. The value of absorbance was converted into the number of cells using a previously prepared analytic curve of the number of cells/absorbance.

Example 1

1. Production of Soluble Collagen from Fish Skin (1) Defatting of Salmon Skin

The skin of a salmon (white salmon, scientific name: *Oncorhynchus Keta*) was used as fish skin. Scales and muscles were removed from the skin using a surgical knife and the remainder was then cut into pieces of about 3 cm square. The pieces were subjected to defatting with an equivolume mixture solvent of chloroform/methanol three times and then washed with methanol twice to remove chloroform, followed by washing three times with water. After that, all of the steps were carried out at 4° C.

(2) Extraction of Collagen and Digestion with Pepsin

The above defatted salmon skin (130 g) was immersed in 5 L of 0.5 M acetic acid at 4° C. and then left standing for 4 days. The swelled salmon skin was filtered through medical gauze and then the filtrate was centrifuged at 10,000×g for 30 minutes to precipitate an insoluble product and 1.5 L a supernatant was collected. The supernatant was mixed with 50 mg of pepsin powder and then stirred gently for 2 days.

(3) Purification of Collagen

Sodium chloride was added to the above collagen solution so as to be a final concentration of 5% and the whole was stirred with a glass rod gently for one minute, followed by leaving at rest for 24 hours. A white insoluble product caused by salt out was centrifuged (under the same condition as that described above) and then the resulting precipitate was collected. The precipitate was added to 2 L of 0.5 M acetic acid and the whole was then stirred gently. Three days were required for completing the dissolution.

This procedure was repeated once and then a transparent collagen solution was obtained. This collagen solution was dialyzed for deionized water using a cellulose tube. Deionized water was changed repeatedly until the pH value of an dialysis external solution showed the neutrality, and then the resulting neutralized solution was freeze-dried. Consequently, white sponge-like collagen was obtained.

2. Preparation of Collagen Gel (1) Preparation of 0.50% Collagen Aqueous Solution The above sponge-like collagen was dried under reduced pressure in a desiccator with silica gel and added with dilute hydrochloric acid (pH 3.0) previously cooled at 4° C. so as to be 0.50 (w/v)% using such a testing value, followed by being dissolved by gentle stirring. Subsequently, the collagen solution was filtered through membrane filters of 10 μM, 0.65 μm, and 0.45 μm in pore size, sequentially. Then filtrate was subdivided into fractions each having a volume of 20 mL into a polypropylene centrifugation tube (50 mL).

(2) Preparation of Aqueous Solution of Cross-Linking Agent

Using a 30 mM sodium phosphate aqueous buffer solution (pH 6.8) containing 70 mM sodium chloride as a solvent, a 100 mM aqueous solution of 1-ethyl-3-(3-dimethylaminopropyl) carbodiimide/hydrochloride was prepared. The resulting aqueous solution of a cross-linking agent was subdivided into fractions each having a volume of 20 mL into a polypropylene centrifugation tube (50 mL).

(3) Preparation of Collagen Gel

All of the steps described below were carried out at 4° C. A centrifugal tube containing the above 0.50% collagen aqueous solution (20 mL) was added with the above cross-linking agent solution (20 mL) and then covered with a lid. The centrifugal tube was shaken to mix the solution, and the solution was flown into a cell-culture polystyrene petridish of 35 mm inner diameter and a glass test tube of 15 mm inner diameter, followed by leaving at rest for 24 hours to obtain a collagen gel.

3. Fiber Structure and Physical Properties of Collagen Gel

Figure 1:
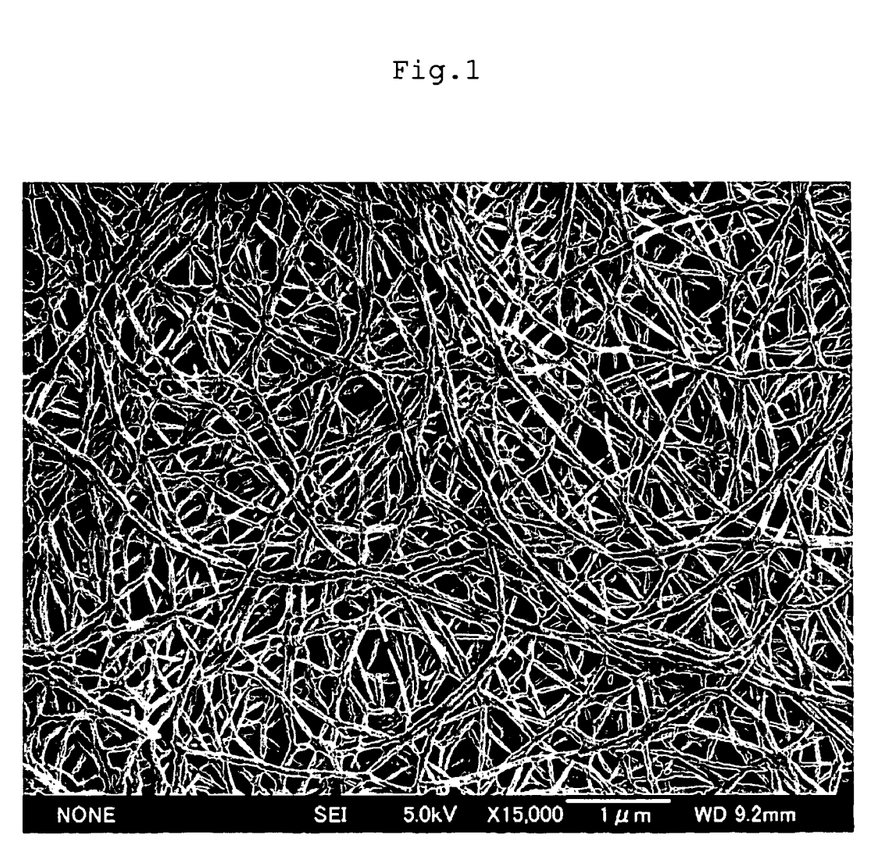
FIG. 1 shows an SEM of collagen fibers in the collagen gel of Example 1.

The collagen fiber structure of a collagen gel observed by an SEM is shown in FIG. 1 and the results of measurement of gel strength and melting point are shown in Table 1.

4. Cell Proliferation Assay on Collagen Gel

Figure 4:
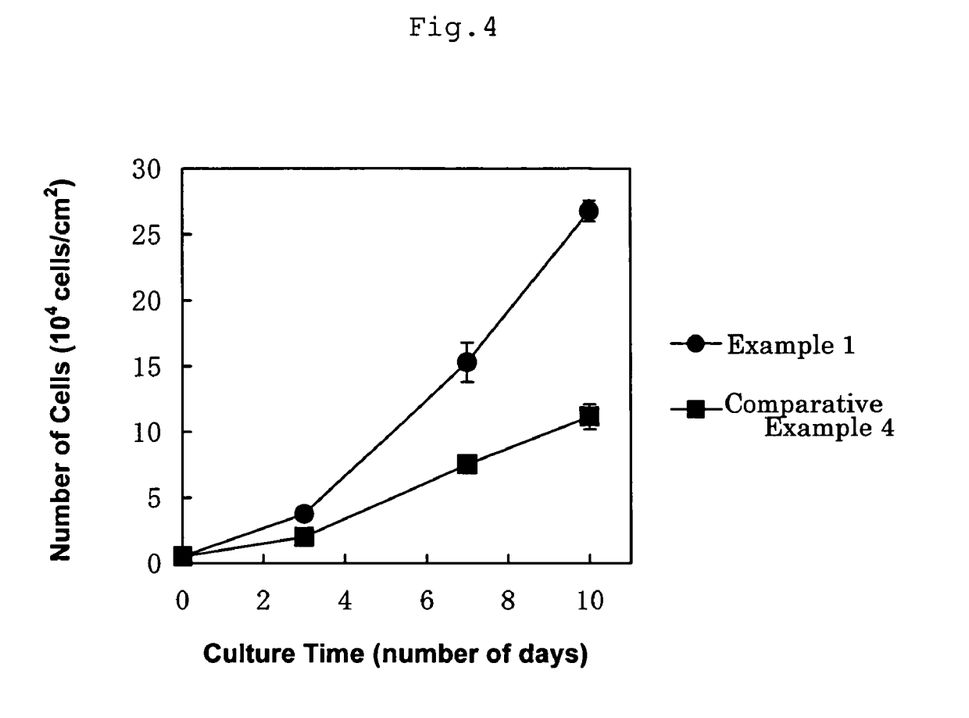
FIG. 4 shows results of cell proliferation assays on the collagen gels in Example 1 and Comparative Example 4.

The results of the cell proliferation assay on a collagen gel are shown in FIG. 4.

Comparative Example 1

A collagen gel was prepared by the same way as that of Example 1, except that the cross-linking agent of Example 1 was not used. A collagen fiber structure was observed with an SEM just like in the case of Example 1. The results of the measurement of gel strength and melting point are shown in Table 1.

Comparative Example 2

A collagen gel was prepared by the same way as that of Example 1, except that the concentration of a cross-linking agent in the cross-linking agent aqueous solution of Example 1 was changed to 20 mM. A collagen fiber structure was observed with an SEM just like in the case of Example 1. The results of the measurement of gel strength and melting point are shown in Table 1.

Comparative Example 3

Figure 2:
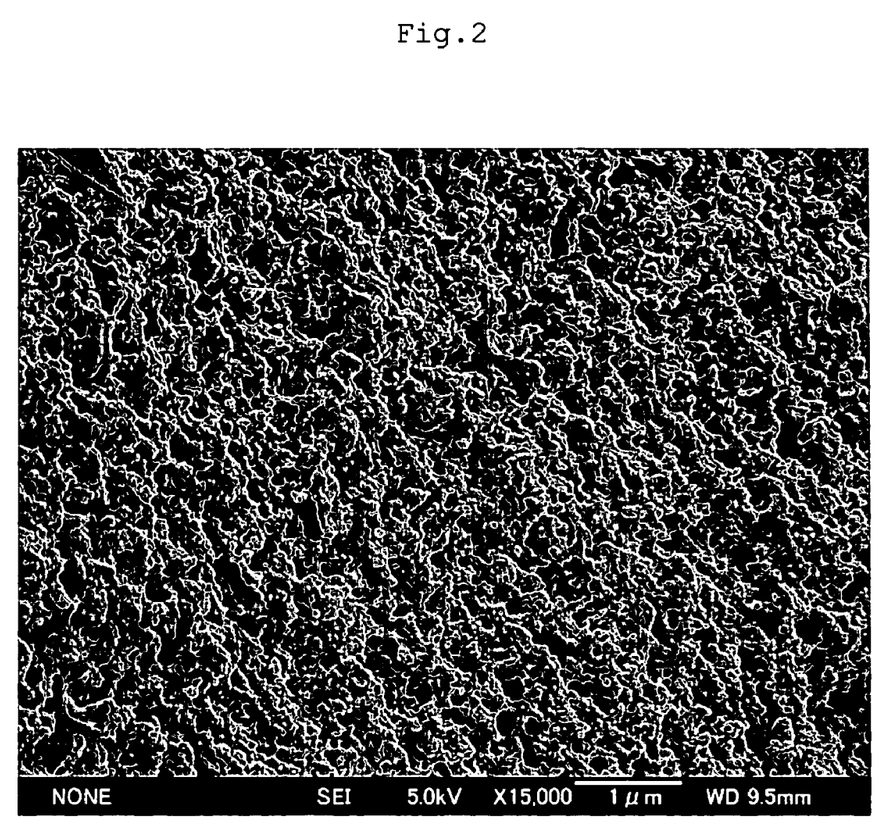
FIG. 2 shows an SEM of collagen fibers in the collagen gel of Comparative Example 3.

A collagen gel was prepared by the same way as that of Example 1, except that the solvent of the cross-linking agent aqueous solution of Example 1 was replaced with deionized water. A collagen fiber structure observed with an SEM is shown in FIG. 2. The results of the measurement of gel strength and melting point are shown in Table 1.

Comparative Example 4

1. Preparation of Collagen Gel 30 ml of a 0.3% aqueous solution of atelocollagen originated from porcine skin (Cellmatrix Type I-P, pH 3 diluted hydrochloric acid solvent, manufactured by Nitta Gelatine) was placed in a centrifugal tube and kept at 4° C. Similarly, 6 ml of 90 mM sodium phosphate buffer aqueous solution (pH 6.8) containing 210 mM sodium chloride kept at 4° C. was added to the centrifugal tube containing the collagen aqueous solution, and the tube was covered with a lid. The centrifugal tube was shaken to mix the solution, and was the solution was flown into a cell-culture polystyrene petridish of 35 mm inner diameter and a glass test tube of 15 mm inner diameter. Then, it was left standing in a 37° C. incubator for 24 hours to obtain a collagen gel.

2. Fiber Structure and Physical Properties of Collagen Gel

Figure 3:
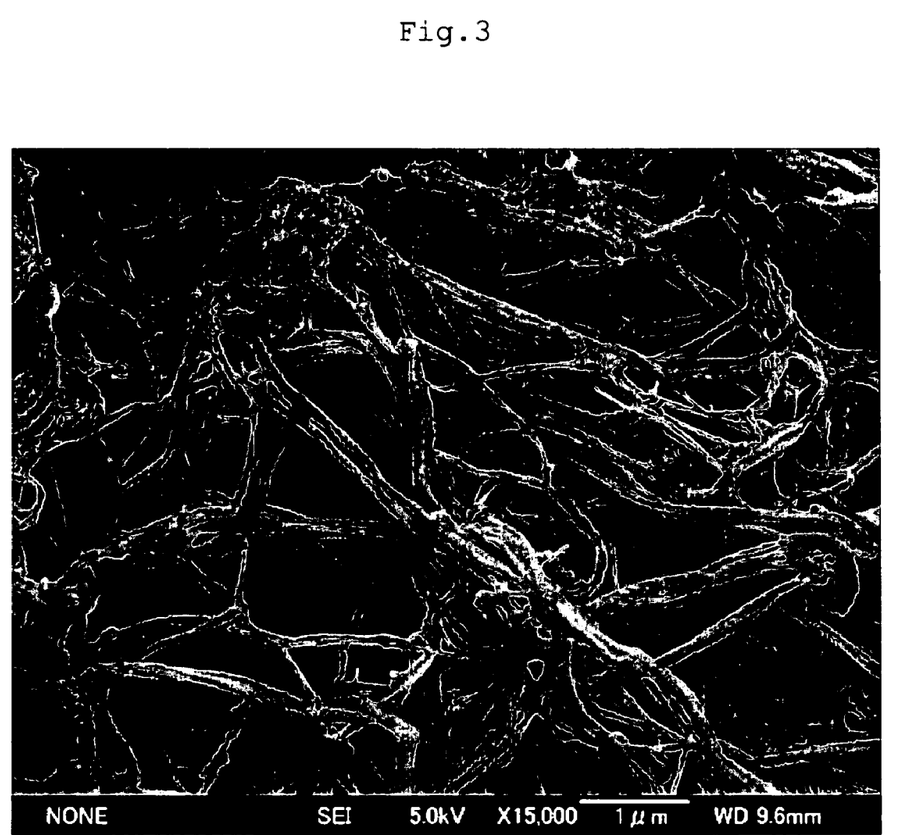
FIG. 3 shows an SEM of collagen fibers in the collagen gel of Comparative Example 4.

The collagen fiber structure of a collagen gel observed by an SEM is shown in FIG. 3 and the results of the measurement of gel strength and melting point are shown in Table 1.

3. Cell Proliferation Assay on Collagen Gel

The results of the cell proliferation assay on a collagen gel are shown in FIG. 4.

TABLE 1

Gel strength and melting point of Collagen Gel

|  | Origin of Collagen | EDC conc. in Gel (mM) | Gel strength (stress; g) | Melting point(° C.) |
|---|---|---|---|---|
| Examples | Salmon | 50 | 1004 | 47 |
| Comparative Example 1 | Salmon | 0 | 114 | 28 |
| Comparative Example 2 | Salmon | 10 | 439 | 32 |
| Comparative Example 3 | Salmon | 50 | 921 | 39 |
| Comparative Example 4 | Pig | 0 | 188 | 47 |

As is apparent from FIG. 1, the collagen gel of the present invention has a collagen fiber structure. As is apparent from Table 1, the production process of the present invention provides the obtained gel with high gel strength and thermal stability with which the gel does not dissolve even at 37° C., body temperature. The thermal stability was equal to that of a gel made from commercial pig-derived atelocollagen of Comparative Example 4. This result shows that oceanic collagen having a low denaturation temperature can be provided with thermal stability at 37° C. which is essential for a medical material.

The collagen gel of the present invention has much higher thermal stability than that of the gel of Comparative Example 3 which does not have a collagen fiber structure at the same cross-linking agent concentration. This result indicates that the process of producing a collagen gel of the present invention is capable of producing a collagen gel having higher thermal stability than that of one obtained by the conventional process of producing a collagen gel.

As is apparent from FIG. 4, cells originated from a human being showed good cell proliferation on the collagen gel of the present invention. The proliferation activity was evidently excellent, compared with that of a gel prepared from a commercial atelocollagen gel originated from porcine skin. This result indicates that the collagen gel of the present invention can be suitably used as a cell culture carrier or a medical material template.

INDUSTRIAL APPLICABILITY

The collagen gel obtained by the process of the present invention is excellent in mechanical strength and thermal stability. Therefore, the collagen gel can be expected to be applied in uses which have been hardly attained by the conventional collagen gel because of its poor strength and insufficient thermal stability. In addition, a collagen gel originated from fishes, which has a low denaturation temperature, can be provided with sufficient thermal stability to be applied in cell carriers or medical materials.

The invention claimed is:

1. A process of producing a collagen gel comprising cross-linked collagen fibrils, said process comprising:
(a) cross-linking collagen fibrils with each other during fibril formation by mixing (i) a collagen solution,
(ii) a cross-linking agent, wherein the collagen does not form fibrils with the cross-linking agent, and
(iii) an aqueous solution of a phosphate, the aqueous solution having a buffering ability, and serving as a solvent, thereby inducing fibril formation and cross-linking occur simultaneously, and
(b) recovering a collagen gel comprising cross-linked collagen fibrils.

2. The process of producing a collagen gel according to claim 1, wherein collagen obtained from fish is used.

3. The process of producing a collagen gel according to claim 1, wherein the cross-linking agent is in the form of a solution prepared by dissolving a water-soluble carbodiimide in the aqueous solution of a phosphate.

4. The process of producing a collagen gel according to claim 1, wherein the collagen solution has a collagen concentration of 0.01 to 3.0 (w/v) %.

5. The process of producing a collagen gel according to claim 1, wherein the cross-linking agent used is in the range of 15 to 80 mM as a final concentration of the cross-linking agent in the collagen gel.

6. The process of producing a collagen gel according to claim 1, wherein mixing the collagen solution with the phosphate solution and with the cross-linking agent is carried out at a temperature lower than the denaturation temperature of the collagen.

7. The process of producing a collagen gel according to claim 6, wherein, after mixing of the collagen solution, the phosphate solution and the cross-linking agent, the resulting mixture is incubated for at least one hour at a temperature lower than the denaturation temperature of the collagen.

8. The process of producing a collagen gel according to claim 1, wherein the cross-linking agent is selected from the group consisting of at least one of the following:
a carbodiimide-based cross-linking agent, an epoxide-based cross-linking agent, an aldehyde-based cross-linking agent and an imidazole-based cross-linking agent.

9. The process of producing a collagen gel according to claim 1, wherein the cross-linking agent is in the form of a water-soluble carbodiimide.

10. The process of producing a collagen gel according to claim 1, consisting of the steps of cross-linking and recovering.

11. A process of producing a collagen gel comprising cross-linked collagen fibrils, said process comprising:
(a) cross-linking collagen fibrils with each other during fibril formation by mixing
(i) a collagen solution, and
(ii) a solution of a cross-linking agent, wherein the collagen does not form fibrils with the cross-linking agent, and, then mixing with the mixture of (i) and (ii)
(iii) an aqueous solution of a phosphate, the aqueous solution having a buffering ability, and serving as a solvent, thereby inducing fibril formation and cross-linking simultaneously, and,
(b) recovering a collagen gel comprising cross-linked collagen fibrils.

* * * * *